United States Patent [19]

Christiansen

[11] Patent Number: 4,610,160

[45] Date of Patent: Sep. 9, 1986

[54] METHOD OF DETERMINING THE MINIMUM LEVEL OF ENRICHMENT FOR A MISCIBLE GAS FLOOD

[75] Inventor: Richard L. Christiansen, Littleton, Colo.

[73] Assignee: Marathon Oil Company, Findlay, Ohio

[21] Appl. No.: 776,724

[22] Filed: Sep. 16, 1985

[51] Int. Cl.⁴ .............................................. G01N 33/26
[52] U.S. Cl. ...................... 73/151; 73/61 R; 73/19; 261/108
[58] Field of Search .................. 73/61 R, 64.4, 19, 53, 73/151; 166/252, 372; 261/108

[56] References Cited

U.S. PATENT DOCUMENTS

| | | | |
|---|---|---|---|
| 3,276,844 | 10/1966 | Davison et al. | 73/64.4 X |
| 3,300,385 | 1/1967 | Danon | 73/53 |
| 4,311,668 | 1/1982 | Solomon | 422/70 |
| 4,395,902 | 8/1983 | Espenscheid et al. | 73/19 |
| 4,455,860 | 6/1984 | Cullick et al. | 73/19 |

OTHER PUBLICATIONS

W. F. Yellig et al., Determination and Prediction of $CO_2$ Minimum Miscibility Pressures, Jour. Petrol. Tech., Jan. 1980, pp. 160–168.

R. L. Christiansen, Minimum Miscibility Pressure (MMP) Apparatus, Technical Disclosure Bulletin, Marathon Oil Company, vol. XXI, Dec. 1981, p. 13.

G. C. Wang, Determination of Miscibility Pressure by Direct-Observation Method, Report DOE/MC/161-40–T2, Jul. 1 to Sep. 30, 1982, pp. 1–13.

*Primary Examiner*—Stephen A. Kreitman
*Assistant Examiner*—Scott M. Oldham
*Attorney, Agent, or Firm*—Jack L. Hummel; Rodney F. Brown

[57] ABSTRACT

A method of determining the minimum level of enrichment required to render a substantially miscible gas miscible in a liquid hydrocarbon by observing the behavior of liquid hydrocarbon droplets as they fall through samples of enriched gas of incrementally increasing levels of enrichment. The lowest level of enrichment at which the droplet is observed to dissipate in the enriched gas is the minimum level of enrichment.

17 Claims, 1 Drawing Figure

METHOD OF DETERMINING THE MINIMUM LEVEL OF ENRICHMENT FOR A MISCIBLE GAS FLOOD

BACKGROUND OF THE INVENTION

1. Technical Field

The invention relates to a method for predetermining the composition of a gas flood used in an enhanced oil recovery process and, more particularly, for determining the minimum level of enrichment required to render a substantially immiscible gas miscible in a crude oil.

2. Description of Related Art

In a gas flood employing a condensing gas drive, intermediate hydrocarbon components in the injected gas condense upon contact with the crude oil in place at the formation temperature and pressure. The condensed hydrocarbon intermediates mix with the crude oil in situ, thereby altering the crude oil composition. If sufficient hydrocarbon intermediates condense from the gas and mix with the oil, the flooding gas and the oil in place ultimately become miscible. This effect is termed a miscible condensing gas drive and it substantially enhances oil recovery from the formation.

Many gases presently employed as flooding gases do not contain sufficient hydrocarbon intermediates to achieve miscibility with the crude oil at formation conditions, i.e., the flooding gases are substantially immiscible in the crude oil. In order to achieve miscibility in the crude oil, it is necessary prior to injection to artificially enrich the flooding gas, termed bulk gas hereafter, with hydrocarbon intermediates contained in an enriching fluid.

The resulting enriched gas is a multicomponent gas comprised of the bulk gas and the enriching fluid. The enriched gas has sufficient hydrocarbon intermediates to render it substantially miscible in the oil upon extended multiple contacting. Since the enriching fluid is often considerably more expensive than the bulk gas, it is desirable to achieve the miscible condensing gas drive using a minimum quantity of the enriching fluid. Thus, determination of the minimum level of enrichment required to render a substantially immiscible gas miscible in a crude oil in place is critical to the operation of a miscible gas flood.

The slim tube method is a widely accepted method for determining the minimum level of enrichment required to render a gas miscible in a crude oil. A slim tube is a long narrow tube approximately 12.2 to 18.3 meters long and having an inside diameter of 0.64 cm or less and packed with an unconsolidated material such as sand or glass beads. The tube is saturated with oil and thereafter flooded with a gas having a given level of enrichment and at constant pressure and temperature. The oil recovery is determined at that level of enrichment and then similar floods are conducted at different levels of enrichment. The oil recovery at each level of enrichment is measured as a function of the volume of gas injected. The oil recovery efficiency is determined thereafter as a function of the enrichment level. The minimum level of enrichment, as determined by the slim tube method, is the level of enrichment above which there is very little increase in oil recovery efficiency. The slim tube method is extremely time-consuming, taking several days to determine the minimum level of enrichment required for a single gas-crude oil system.

As such, an accurate and more rapid method is needed for determining the minimum level of enrichment required for gas used in a miscible condensing gas drive.

SUMMARY OF THE INVENTION

The present invention relates to a method of determining the minimum level of enrichment required to render a substantially immiscible bulk gas miscible in a liquid hydrocarbon. A series of two or more experimental runs are conducted as follows. An enriched gas sample comprised of the bulk gas and an enriching gas, but having a level of enrichment below the minimum level, is charged to a transparent vessel enabling visual observation therein. The enriched gas in the vessel is maintained at a given predetermined pressure and temperature. A liquid hydrocarbon droplet is discharged into the vessel such that the droplet falls under the force of gravity through the enriched gas. The behavior of the droplet is observed as it continuously contacts the enriched gas. When the droplet comes to rest at the bottom of the vessel, the spent gas and droplet are removed.

In the next run the vessel is charged with a fresh enriched gas sample having an incrementally higher level of enrichment. The enriched gas is maintained at the same temperature and pressure as above. A fresh liquid hydrocarbon droplet having the same initial composition as the previous droplet is discharged into the vessel and its behavior is observed in the same manner as above.

The experimental runs are repeated as often as necessary, each time incrementally increasing the level of enrichment of the bulk gas, until the droplet of liquid hydrocarbon is first observed to substantially dissipate in the gas. This point is termed the minimum level of enrichment required to render the bulk gas miscible in the liquid hydrocarbon. At the minimum level, the interfacial tension between the droplet and the gas approaches zero, causing the droplet to dissipate in a characteristic manner in the gas.

The present method quickly and accurately enables one to determine the minimum level of enrichment required to render substantially any immiscible liquid miscible in substantially any gas simulating the multiple contact miscibility mechanism believed to occur in an oil-bearing subterranean formation. Determination of an accurate minimum level of enrichment enables one to optimize the cost and oil recovery efficiency of a miscible gas flood using a condensing gas drive.

DESCRIPTION OF THE PREFERRED EMBODIMENTS

Figure 1:
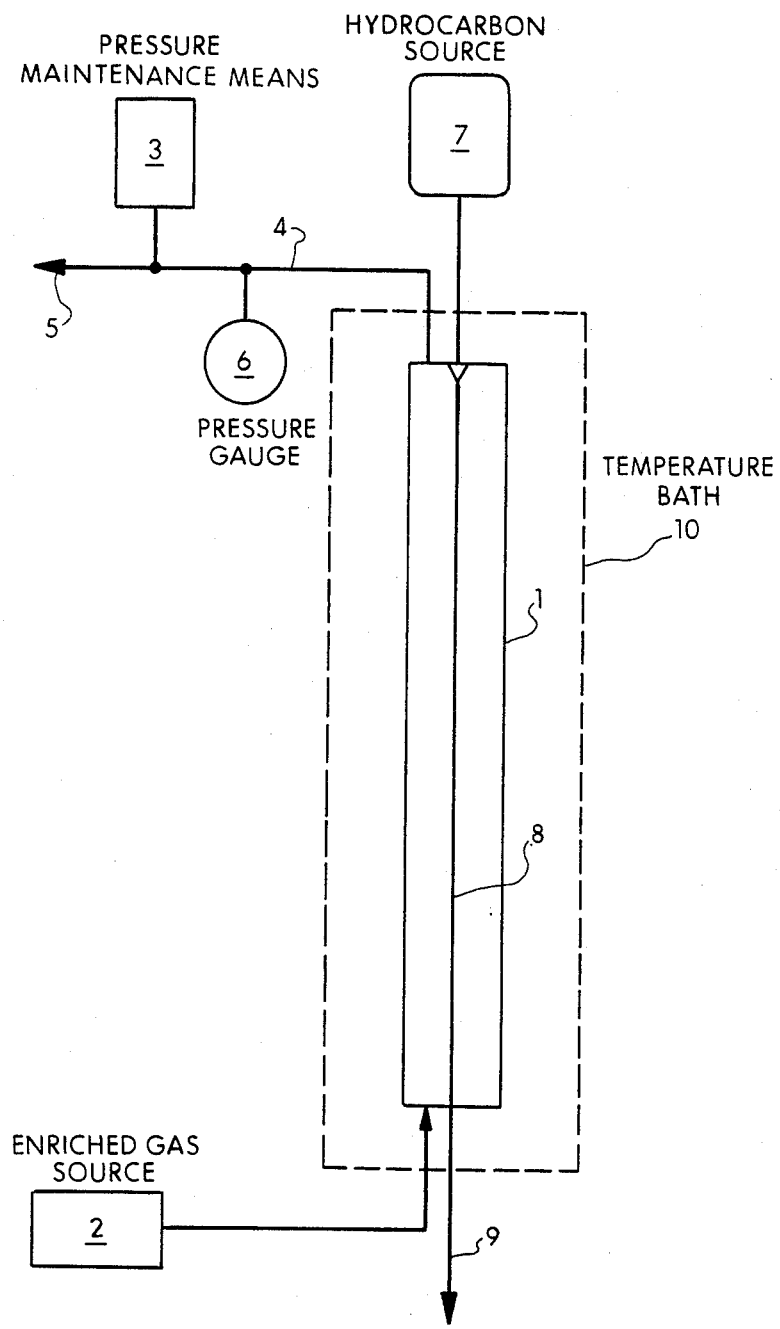
FIG. 1 is a schematic drawing of the present method.

The minimum level of enrichment is defined as the level of gas enrichment at which the interfacial tension at an interface between a liquid droplet and a continuous enriched gas approaches zero, causing the liquid droplet to substantially dissipate in the gas. In practice, the interfacial tension at the interface between the droplet and the gas is not exactly zero at the minimum level of enrichment because a number of fluid mechanic effects may cause the droplet to dissipate before an interfacial tension of exactly zero is reached. However, for practical purposes the sum of the effects are very small relative to the interfacial tension. Thus, an interfacial tension of zero at the minimum level of enrichment is a good approximation.

The liquid forming the droplet is a hydrocarbon. The liquid hydrocarbon is preferably a crude oil obtained from a subterranean oil-bearing formation of interest.

The enriched gas described herein is comprised of a bulk gas and an enriching fluid. The bulk gas is substantially any gas which has a minimum miscibility pressure in the liquid hydrocarbon above the formation fracturing pressure or the anticipated operating pressure of a flood at the formation temperature. Examples of the bulk gas include $CO_2$, $N_2$ and lean natural gas, i.e., methane.

The enriching fluid is an intermediate hydrocarbon, i.e., a hydrocarbon having a molecular weight greater than methane and preferably less than decane. Such fluids include ethane, propane, butane, etc., and mixtures thereof. The enriching fluids are often liquids as pure components. However, when the enriching fluid is a component of the enriched gas, it remains in the gas phase until it contacts the liquid hydrocarbon. The enriching fluid is substantially miscible in the bulk gas and is preferably more miscible than the bulk gas in the liquid hydrocarbon due to a lower miscibility pressure.

The present method as depicted in FIG. 1 comprises preparing an enriched gas sample having a level of enrichment below the minimum level. The enriched gas is charged to a transparent glass vessel 1 from an enriched gas source 2. The enriched gas may be prepared metering the enriching fluid and bulk gas from separate sources into a common line and mixing them in-line. Alternatively, a number of enriched gas samples having different levels of enrichment can be premixed in individual sample tanks. A separate sample tank containing premixed enriched gas as shown in FIG. 1 is used for each run as the enriched gas source 2.

A pressure maintenance means 3, which may be a piston, fluid head or the like, pressurizes the contents of the vessel to a predetermined operating pressure which preferably corresponds to the anticipated pressure of a gas flood of interest. This pressure is generally limited to a pressure range below the fracturing pressure of the formation to be flooded. The pressure maintenance means 3 is in fluid communication with the vessel via a pressurizing line 4, having an outlet 5 which also serves as a spent gas vent. A pressure gauge 6 may be placed in the line to monitor the pressure. A temperature maintenance means 10, such as a temperature bath shown here, surrounds the vessel and maintains the temperature of the vessel and its contents at the temperature of the formation to be flooded.

The liquid hydrocarbon is stored in a hydrocarbon source 7 in fluid communication with the vessel. A sample obtained from the liquid hydrocarbon source is formed into a droplet at the top of the vessel. The liquid hydrocarbon droplet is released into the gas contained by the vessel and falls downward under the force of gravity through the gas. The droplet continuously contacts the gas on its downward path. The behavior of the droplet is observed visually along its path. The falling droplet may be photographed by still, motion picture, or video camera. The experimental run concludes when the droplet comes to rest at the bottom of the vessel.

The droplet's path of fall may be directed by a filament 8 suspended in the interior of the vessel from the droplet release point to the bottom of the vessel. The filament is preferably comprised of a material which does not absorb the liquid hydrocarbon such as a fine metal wire or glass. The liquid droplet is formed around the top of the filament and slides along the filament to the bottom of the vessel. The filament can be aligned at an angle 90° from the horizontal or alternatively it can be aligned at an angle less than 90° from the horizontal such that the path of the droplet is not exactly vertical. The alignment angle of the filament controls the rate at which the droplet falls thereby controlling the contact time between the droplet and enriched gas. The contact time can also be controlled by selecting the material of the filament to have a desired surface tension between it and the droplet.

After the initial experimental run, the spent gas and liquid hydrocarbon samples are expelled from the vessel via gas vent 5 and a spent liquid hydrocarbon line 9 respectively. A fresh enriched gas sample, which has an incrementally higher level of enrichment, is charged to the vessel in the same manner as above. The contents of the vessel are maintained at the same pressure and temperature as the initial run. A droplet is formed from a fresh liquid hydrocarbon sample which is substantially identical in composition and volume to the sample of the initial run. The procedure of the initial run is then repeated and the behavior of the droplet observed.

The procedure is repeated as often as necessary, each time incrementally increasing the level of enrichment, until the liquid hydrocarbon droplet is observed to substantially dissipate in the gas before it reaches the bottom of the vessel. By substantially dissipate it is meant that the droplet spontaneously shrinks to a significantly smaller visible volume or the droplet completely vaporizes and is not visible at all. The level of gas enrichment in the run where dissipation occurs is observed to be the minimum level of enrichment required to render the substantially immiscible bulk gas miscible in the liquid hydrocarbon. The value for the minimum level of enrichment so determined is utilized by the skilled practitioner to design a miscible condensing gas drive.

The mechanism by which it is believed the liquid hydrocarbon becomes miscible in the enriched gas is termed multiple contact miscibility. According to this mechanism, the gas initially contacted by the liquid droplet in the vessel is fresh enriched gas containing intermediate hydrocarbon components. Although the gas and liquid are not immediately miscible upon first contact, the intermediate hydrocarbon components in the gas condense on first contact with the droplet. The condensed components migrate by mass transfer across the interface between the droplet and the gas into the droplet. As the condensed hydrocarbon components migrate into the droplet, they change the composition of the droplet. The liquid hydrocarbon droplet falls through the enriched gas, continuously contacting fresh gas, continuously accepting intermediate hydrocarbon components, and leaving behind the gas stripped of intermediate hydrocarbon components. At the minimum level of enrichment, a sufficient quantity of hydrocarbon components enters the droplet to finally render it miscible in the gas and the droplet substantially dissipates. As used herein, where fluids are termed "miscible" or "immiscible" in the liquid hydrocarbon, they are referred to as such in the context of a multiple contact miscibility mechanism.

The following examples are illustrative of the method of the present invention but are not to be construed as limiting the scope thereof.

EXAMPLE 1

The minimum level of enrichment required to render an enriched gas comprised of a methane bulk gas and an n-butane enriching fluid in liquid decane is determined according to the following method. Methane, which is substantially immiscible in decane at the desired conditions, is enriched with n-butane to a level below the minimum level of enrichment. A sample of the enriched methane is charged to a transparent glass vessel and maintained at a temperature of 71° C. and a pressure of 20700 kPa. A droplet of decane is formed on a metal wire suspended from the top of the vessel and discharged into the enriched methane. The behavior of the droplet is observed as it slides along the wire until it comes to rest at the bottom of the vessel. The stripped enriched gas and droplet are then discharged from the vessel and the experiment is repeated with a fresh enriched methane sample having an incrementally higher level than the first sample. The results of these and succeeding runs are shown in Table 1 below.

TABLE 1

| Enriched Gas Composition (mole fraction) | | |
|---|---|---|
| Methane | n-Butane | Observations |
| 0.92 | 0.08 | Droplet slowly shrinks while sliding down wire. |
| 0.88 | 0.12 | Droplet slowly shrinks while sliding down wire. |
| 0.84 | 0.16 | Drop first swells while sliding down wire then rapidly vaporizes. |
| 0.80 | 0.20 | Drop first swells while sliding down wire then rapidly vaporizes. |

The minimum level of enrichment required to render methane miscible in decane by a multiple contact miscibility mechanism at the stated temperature and pressure conditions is experimentally determined to be a 0.16 mole fraction n-butane in methane. This is the lowest level of enrichment at which the decane droplet is observed to dissipate in the enriched methane.

EXAMPLE 2

The minimum level of enrichment required to render an enriched gas comprised of a methane bulk gas and an ethane enriching gas in a crude oil at 116° C. and 34500 kPa is determined according to the method of Example 1. The crude oil has an API specific gravity of 35, bubblepoint pressure of 13400 kPa and a gas-oil ratio of 400 standard cubic feet per stock tank barrel. The results are shown below in Table 2.

TABLE 2

| Enriched Gas Composition (mole fraction) | | |
|---|---|---|
| Methane | Ethane | Observations |
| 0.91 | 0.09 | Droplet slowly shrinks while sliding down wire. |
| 0.88 | 0.12 | Drop rapidly vaporizes after sliding a short distance down wire. |
| 0.83 | 0.17 | Drop rapidly vaporizes after sliding a short distance down wire. |

The minimum level of enrichment required to render the methane miscible in the crude oil is determined to be a 0.12 mole fraction ethane in methane.

While the foregoing preferred embodiment of the invention has been described and shown, it is understood that the alternatives and modifications, such as those suggested and others, may be made thereto and fall within the scope of the invention.

I claim:

1. A method for determining the minimum level of enrichment required to render a substantially immiscible bulk gas miscible in a liquid hydrocarbon comprising the steps of:
    (a) charging a sample of an enriched gas comprised of said bulk gas and an enriching fluid wherein the level of enrichment of said enriched gas is substantially below said minimum level of enrichment to a transparent vessel;
    (b) maintaining said sample of enriched gas at a predetermined substantially constant temperature and pressure;
    (c) discharging a droplet comprised of said liquid hydrocarbon into said vessel such that said droplet falls through said enriched gas in said vessel while continuously and visibly contacting said enriched gas;
    (d) observing the behavior of said droplet as it contacts said enriched gas;
    (e) withdrawing said droplet and enriched gas from said vessel after said droplet has come to rest in said vessel;
    (f) charging a fresh sample of said enriched gas having an incrementally higher level of enrichment than said previous sample to said vessel;
    (g) repeating steps b–f, each time incrementally increasing the level of enrichment of said fresh sample over said previous sample, until said droplet is first observed to substantially dissipate in said enriched gas at a given level of enrichment; and
    (h) determining said given level of enrichment at which said droplet substantially dissipates in said enriched gas to be said minimum level of enrichment required to render said bulk gas miscible in said liquid hydrocarbon.

2. The method of claim 1 wherein said droplet is discharged onto a filament suspended within said vessel such that said droplet follows the path of said filament as it continuously contacts said enriched gas.

3. The method of claim 2 wherein substantially no liquid hydrocarbon or enriched gas absorbs on said filament.

4. The method of claim 1 wherein said liquid hydrocarbon is a crude oil.

5. The method of claim 1 wherein said bulk gas is substantially less miscible than said enriching fluid in said liquid hydrocarbon.

6. The method of claim 1 wherein said bulk gas is selected from the group consisting of carbon dioxide, nitrogen, methane, and mixtures thereof.

7. The method of claim 1 wherein said enriching fluid is selected from the group consisting of ethane, propane, butane, pentane, and mixtures thereof.

8. The method of claim 2 wherein said filament is selected such that the surface tension between said droplet and filament predetermines a desired contact time of said droplet with said enriched gas.

9. The method of claim 2 wherein said filament is aligned in said vessel at an angle from the horizontal to predetermine a desired contact time of said droplet with said enriched gas.

10. The method of claim 1 wherein said enriching fluid is substantially miscible in said bulk gas at said substantially constant temperature and pressure.

11. A method for predetermining the minimum level of enrichment required for an enriched gas to sustain a miscible condensing gas drive for the recovery of a crude oil from a subterranean oil-bearing formation having a temperature and a fracturing pressure, comprising the steps of:
   (a) charging a sample of said enriched gas comprised of a bulk gas and an enriching fluid wherein the level of enrichment of said enriched gas is substantially below said minimum level of enrichment to a transparent vessel;
   (b) maintaining said sample of enriched gas at said substantially constant formation temperature and a pressure substantially below said formation fracturing pressure;
   (c) discharging a droplet comprised of said crude oil obtained from said formation into said vessel such that said droplet falls through said enriched gas in said vessel while continuously and visibly contacting said enriched gas;
   (d) observing the behavior of said droplet as it contacts said enriched gas;
   (e) withdrawing said droplet and enriched gas from said vessel after said droplet has come to rest in said vessel;
   (f) charging a fresh sample of said enriched gas having an incrementally higher level of enrichment than said previous sample to said vessel;
   (g) repeating steps b-f, each time incrementally increasing the level of enrichment of said fresh sample over said previous sample, until said droplet is first observed to substantially dissipate in said enriched gas at a given level of enrichment; and
   (h) determining said given level of enrichment at which said droplet substantially dissipates in said enriched gas to be said minimum level of enrichment required for said enriched gas to sustain said miscible condensing gas drive for the recovery of said crude oil from said subterranean oil-bearing formation.

12. The method of claim 11 wherein said droplet is discharged onto a filament suspended within said vessel such that said droplet follows the path of said filament as it continuously contacts said enriched gas.

13. The method of claim 11 wherein said bulk gas is substantially less miscible than said enriching fluid in said liquid hydrocarbon.

14. The method of claim 11 wherein said bulk gas is selected from the group consisting of carbon dioxide, nitrogen, methane, and mixture thereof.

15. The method of claim 11 wherein said enriching fluid is selected from the group consisting of ethane, propane, butane, pentane, and mixtures thereof.

16. The method of claim 12 wherein said filament is aligned in said vessel at an angle from the horizontal to predetermine a desired contact time of said droplet with said enriched gas.

17. The method of claim 11 wherein said enriching fluid is substantially miscible in said bulk gas at said substantially constant formation temperature and said pressure below said formation fracturing pressure.

* * * * *

UNITED STATES PATENT AND TRADEMARK OFFICE
CERTIFICATE OF CORRECTION

PATENT NO. :     4,610,160

DATED      :     September 9, 1986

INVENTOR(S) :    Richard L. Christiansen

It is certified that error appears in the above-identified patent and that said Letters Patent is hereby corrected as shown below:

Abstract, line 2:     Delete "miscible gas" and insert --immiscible gas--.

Signed and Sealed this

Twenty-eighth Day of November 1989

Attest:

JEFFREY M. SAMUELS

*Attesting Officer*     *Acting Commissioner of Patents and Trademarks*